United States Patent [19]

dePadova

[11] Patent Number: 5,464,854
[45] Date of Patent: Nov. 7, 1995

[54] METHOD OF MODIFYING OVARIAN HORMONE-REGULATED AT1 RECEPTOR ACTIVITY AS TREATMENT OF INCAPACITATING SYMPTOM(S) OF P.M.S.

[76] Inventor: Anathony S. dePadova, 49 Dexter Dr., North, Basking Ridge, N.J. 07920

[21] Appl. No.: 235,468

[22] Filed: Apr. 29, 1994

Related U.S. Application Data

[63] Continuation-in-part of Ser. No. 145,147, Nov. 11, 1993.
[51] Int. Cl.[6] .......................... A61K 31/54; A61K 31/44; A61K 31/41; A61K 31/415; A61K 31/40
[52] U.S. Cl. .......................... 514/381; 514/303; 514/394; 514/397; 514/417; 514/223.5
[58] Field of Search ..................... 514/303, 381, 514/394, 397, 223.5, 417

[56] References Cited

U.S. PATENT DOCUMENTS

| | | | |
|---|---|---|---|
| 4,912,096 | 3/1990 | Sudilovsky | 514/91 |
| 4,931,430 | 6/1990 | Sudilovsky et al. | 514/19 |
| 5,246,943 | 9/1993 | Blankley et al. | 514/307 |

OTHER PUBLICATIONS

Conn's Current Therapy, 1992, pp. 1014–1017.

*Primary Examiner*—Kimberly R. Jordan
*Attorney, Agent, or Firm*—Hoffmann & Baron

[57] ABSTRACT

The method of treatment moderating, blocking and/or eliminating premenstrual syndrome embodies the intermittent administering of an AT1 antagonist to a female having menstrual cycles characterized predominately by during substantially the luteal phase inclusive of at least one and frequently by two or more affective and/or autonomic and/or somatic symptoms of substantially incapacitating severity(ies) proximately substantially prior to menses of a menstrual cycle. Losartan is an example of an AT1 inhibitor and is administered either orally or parenterally continuously to a female during her menstrual cycle's luteal phase.

7 Claims, 9 Drawing Sheets

| FUNCTION | INPUT/COORDINATION AREA | RECEPTOR |
|---|---|---|
| TEMPERATURE | ANTERIOR & POSTERIOR HYPOTHALAMUS | $AT_1$ |
| NEUROENDOCRINE CONTROL OF: CATECHOLAMINES/SYMPATHETIC (AUTONOMIC CONTROL) | EMOTIONAL STIMULI VIA LIMBIC SYSTEM, DORSOMEDIAL AND POSTERIOR HYPOTHALAMUS LATERAL HYPOTHALAMUS | ANG II $AT_1$ $AT_1$ |
| VASOPRESSIN (ADH) | SUPRAOPTIC/PARAVENTRICULAR | $AT_1$/ANG II |
| LHRH | PREOPTIC AREAS | ANG II/$AT_1$ |
| APPETITE BEHAVIOR, THIRST | SFO, OVLT LATERAL/SUPERIOR/ANTERIOR | $AT_1$/ANG II |
| HUNGER | VENTRO-MEDIAL, SATIETY CENTER, LATERAL - HUNGER CENTER SOME LIMBIC COMPONENTS | $AT_1$/ANG II $AT_1$ ANG II |
| DEFENSIVE BEHAVIOR: FEAR, RAGE, MOTIVATION | LIMBIC SYSTEM (AMYGDALA/HIPPOCAMPUS) MIDBRAIN, LATERAL AND VENTROMEDIAL AREAS | ANG II $AT_1$ |

FIG-8

| HYPOTHALAMIC FUNCTION | PMS SYMPTOMS |
|---|---|
| HUNGER, APPETITE BEHAVIOR, THIRST VASOPRESSIN | ANOREXIA, ABNORMAL FOOD CRAVINGS, CHANGES IN APPETITE, BLOATING, EDEMA |
| DEFENSIVE BEHAVIOR, FEAR, RAGE, MOTIVATION | IRRATIONAL BEHAVIOR, IRRITABILITY, LABILE MOOD, ANGER, DECREASED MOTIVATION |
| AUTONOMIC CONTROL | HOT/COLD FLASHES, PALPITATIONS, NAUSEA, SWEATING, SYNCOPE, GENERAL ACHES AND PAINS |

| | 1 | 2 | 3 | 4 | 5 | | 35 | 36 | 37 | 38 | 39 | 40 |
|---|---|---|---|---|---|---|---|---|---|---|---|---|
| BLEEDING | | | | | | | | | | | | |
| DY OF MENSTRUAL CYCLE | 1 | 2 | 3 | 4 | 5 | | 35 | 36 | 37 | 38 | 39 | 40 |
| MONTH:    DATE: | | | | | | | | | | | | |
| WEIGHT CHANGE | | | | | | | | | | | | |
| SYMPTOMS | | | | | | | | | | | | |
| IRRITABLE | | | | | | | | | | | | |
| FATIGUE | | | | | | | | | | | | |
| INWARD ANGER | | | | | | | | | | | | |
| LABILE MOOD (CRYING) | | | | | | | | | | | | |
| DEPRESSED | | | | | | | | | | | | |
| RESTLESS | | | | | | | | | | | | |
| ANXIOUS | | | | | | | | | | | | |
| INSOMNIA | | | | | | | | | | | | |
| LACK OF CONTROL | | | | | | | | | | | | |
| EDEMA OR RINGS TIGHT | | | | | | | | | | | | |
| BREAST TENDERNESS | | | | | | | | | | | | |
| ABDOMINAL BLOATING | | | | | | | | | | | | |
| BOWELS: CONST. (C) LOOSE (L) | | | | | | | | | | | | |
| APPETITE: UP   DOWN | | | | | | | | | | | | |
| SEX DRIVE: UP   DOWN | | | | | | | | | | | | |
| CHILLS (C) SWEATS (S) | | | | | | | | | | | | |
| HEADACHES | | | | | | | | | | | | |
| CRAVE: SWEETS, SALT | | | | | | | | | | | | |
| FEEL UNATTRACTIVE | | | | | | | | | | | | |
| GUILTY | | | | | | | | | | | | |
| UNREASONABLE BEHAVIOR | | | | | | | | | | | | |
| LOW SELF IMAGE | | | | | | | | | | | | |
| NAUSEA | | | | | | | | | | | | |
| MENSTRUAL CRAMPS | | | | | | | | | | | | |
| LIFESTYLE IMPACT | | | | | | | | | | | | |
| AGRESSIVE TOWARDS OTHERS — PHYSICALLY | | | | | | | | | | | | |
| AGRESSIVE TOWARDS OTHERS — VERBALLY | | | | | | | | | | | | |
| WISH TO BE ALONE | | | | | | | | | | | | |
| NEGLECT HOUSEWORK | | | | | | | | | | | | |
| TIME OFF WORK | | | | | | | | | | | | |
| DISORGANIZED, DISTRACTABLE | | | | | | | | | | | | |
| ACCIDENT PRONE/CLUMSY | | | | | | | | | | | | |
| UNEASY ABOUT DRIVING | | | | | | | | | | | | |
| SUICIDAL THOUGHTS | | | | | | | | | | | | |
| STAYED AT HOME | | | | | | | | | | | | |
| INCREASED USE OF ALCOHOL | | | | | | | | | | | | |
| LIFE EVENTS | | | | | | | | | | | | |
| NEGATIVE EXPERIENCE | | | | | | | | | | | | |
| POSITIVE EXPERIENCE | | | | | | | | | | | | |
| SOCIAL ACTIVITIES | | | | | | | | | | | | |
| VIGOROUS EXERCISE | | | | | | | | | | | | |
| MEDICATIONS | | | | | | | | | | | | |

METHOD OF MODIFYING OVARIAN HORMONE-REGULATED AT1 RECEPTOR ACTIVITY AS TREATMENT OF INCAPACITATING SYMPTOM(S) OF P.M.S.

This invention is directed to a method of treatment for obviating and/or blocking premenstrual tension syndrome on an interim basis during the luteal phase of a menstrual cycle of a patient suffering from premenstrual syndrome characterized by a concurrent plurality of symptoms inclusive of affectlye and/or autonomic and/or somatic symptoms cumulatively of substantially incapacitating severity prior to the menses. This is a continuation-in-part of U.S. Ser. No. 08/145,147 filed Nov. 11, 1993, now pending, incorporated by reference into this disclosure.

PRIOR ART

United States Patent to Blankley, C. J., et. al., U.S. Pat. No. 5,246,943 granted Sep. 21, 1993 states in sections 3 line 40 that "excessive secretion of AVP (vasopressin, also known as antidiuretic hormone) as been linked to a number of disorders including excessive water retention associated with the female reproductive disorder known as premenstrual syndrome (PMS) (Janowski, et.al., Psychosomatic Medicine 35:143–154 (1973)". The authors claim that compounds which block angiotensin II subtype 2 (AT2) receptors induced AVP secretion are therefore, useful in treating the above disorders. The abovementioned article of Janowsky does not suggest nor even specifically mention AVP as a cause of PMS. Janowski, et. al. describes an increase in the retention of sodium (Na) with a subsequent retention of water. Janowski, et. al. correlated the similarity of their findings to the physiologically known effects of aldosterone. In fact, a rise in body sodium would cause a decrease in AVP secretion. Ganong, W. F., in his textbook of physiology (1987) clearly states on Page 607, "the amount of sodium in the ECF (extracellular fluid) is the most important determinant of ECF volume . . . rise in ECF volume inhibits vasopressin (AVP) secretion. Volume stimuli override the osmotic regulation of vasopressin secretion." More importantly, is the fact that no correlation exists between circulating levels or changes in circulating levels of AVP aldosterone or any other hormone and the appearance of the symptoms of PMS. (Reid, R. L.: Premenstrual Syndrome: Current Problems in Obstetrics, Gynecology and Fertility, February, Vol. VIII, No. 2, 1985). Additionally when an AT2 receptor antagonist (PD123319) was administered to dogs, it had no effect on circulating vasopressin levels. (Keiser, J. A., et. al., *Renal Hemodynamic and Excretory Responses to PD123319 and Losartan Nonpeptide AT1 and AT2 Subtype Specific Angiotension II ligands*, J. Pharmacol. Exp. Ther., September 1992; 263(3): 1154–60. In addition, there are no differences in any of the measured hormonal changes between PMS and non-PMS patient.

In addition, Blankley, et. al. in section 2, line 51 declare that their invention refers specifically to agents that block the angiotension II subtype 2 (AT2) receptors found in the central nervous system of mammals and the compounds described are supposedly effective in blocking only the binding of angiotension II (Ang II) at AT2 receptors. They claim that various disorders including neurologic, psychiatric, neuroendocrine, neurodegenerative and neuroimmunological disorders including addiction, anxiety, depression, epilepsy, hyperactivity, memory, pain, psychosis, regulation of autonomic functions and sleep are included in their patent only when regulated by AT2 receptors. A study evaluating the effects of blocking AT1 and AT2 receptors on sympathetic (autonomic) nervous system function and effects of intravenously administered norepenephrine (NE) showed that blocking the subtype 2 receptor (using PD123177) did not modify the effects of intravenous NE nor modify effects of sympathetic nervous system stimulation, thus showing that there are distinct differences in the effects of these different receptors in regulating antonomic functions and therefore, clearly separting the present invention from the prior art (Wong, P. C., et. al., *Effect of Blocking Angiotension II Receptor Subtype on Rat Sympathetic Nerve Function*, Hypertension, January 1992; 19(6PT2): 663–7).

BACKGROUND TO THE INVENTION

The accepted medical characterization and definition for women of an age inclusive of periodically recurring menstrual cycles, of the syndrome commonly is referred to as premenstrual tension syndrome. PMS is a group of symptoms that occur together almost entirely or principally during the intermittent luteal phase of a menstrual cycle; those intermittent periodic luteal phase-occurring symptoms that characterize a PMS abnormality, are a plurality of at least two or more (normally many) of physical, psychological and/or behavioral symptoms of combined substantially incapacitating severity to an extent requiring treatment in order for the affected woman-subject to continue to function normally socially and/or occupationally of conventional daily activities during that luteal phase.

The periodic intermittently reoccurring symptoms of PMS match the phases of a woman's menstrual cycle, occurring normally and principally in the menstrual cycle's luteal phase which by medical definition occurs after ovulation with PMS symptoms normally beginning at, or near the end of or shortly after the follicular (egg development) stage and lasting to about the beginning of the menses (bleeding) stage of the menstrual cycle.

As shall be more particularly pointed out below, the method of the present invention of PMS treatment utilizes solely and exclusively angiotensin II subtype 1 (AT1) antagonists, and the foregoing noted prior art of the U.S. Pat. No. 5,246,943 to Blankley, et. al does not apply nor even refer to the presence of the AT1 receptors located in the subfornical organ (SFO), organism vasculosum of the lamina terminalis, median preoptic nucleus, nucleus of the solitary tract, the area postrema nucleus of the hypothalamus and ventral hippocampus which contain almost exclusively AT1 receptors. (Rowe, B. P. et. al. "Analyses of Angiotensin II Receptor Subtypes in Individual Rat Brain Nuclei, Neuroendocrinology: 1992;55:563–573). In addition, the Blankley et. al. patent states that their interest is to treat the aspect of PMS described as the "disorder of excessive water retention" and therefore does not refer to the premenstrual syndrome of multiple physical psychological and/or behavioral symptoms as described briefly above and to be further elucidated subsequently. Apart from that, *The Conn's Current Therapy.*, Premenstrual Syndrome above-noted, at Page 1016 thereof, column 1 at the last paragraph explicitly states that no consistent relief appears to be provided by "diuretics", a class of drugs known to promote the loss of water.

U.S. Pat. No. 5,246,943 granted Sep. 21, 1993 to Blankley, et. al. discloses a series of angiotensin antagonists directed at the subtype 2 receptors, and is directed only at symptoms mediated by these receptors in the central nervous system. Accordingly, the Blankely, et. al., U.S. Pat. No. 5,246,943 has no relevance to and clearly does not suggest nor make logical the present invention relating to PMS symptoms divergent and not in the least comparable to those described in the aforestated patent, which is directed at AT2 receptors in the CNS and limited in its meaning having no reasonable common basis with menstrual luteal phase PMS symptoms intermittently recurring and associated directly with the luteal phase and regulated as will be described to areas of the CNS containing angiotensin II subtype 1 receptors (AT1). Important is the medically recognized fact that PMS is strictly associated with recurring menstrual cycles and the appearance of PMS symptoms solely and exclusively during the luteal phase. Moreover, it has been experimentally established that such PMS symptoms disappeared when human females were ovariectomized, evidence in a study by R. F. Casper and Hearn. *The effect of hysterectomy and bilateral oophorectomy in women with severe premenstrual syndrome.* Am. J. Obstet. Gynecol. 162:105–9, 1990, and evidenced by females who underwent medical "ovariectomy" by use of a GnRH agonist, which effectively eliminated their menstrual cycle as demonstrated by Muse, K. N., et al. *The premenstrual syndrome: effects of "Medical Ovariectomy"*, N. Engl. J. Med. 311:1,345, 1984. Accordingly, the drug of the present invention, acting AT1) receptors in the CNS and outside the central nervous system (peripherally) and directed to strictly female menstrual cycle's luteal phase of "numerous" (multiple) concurrent PMS symptoms of which perhaps one of numerous required symptoms (in order to be characterized as PMS syndrome) might or might not be present, does "not" embody any suggestion or teaching that would suggest obviousness of the present invention.

OBJECTS OF THE INVENTION

A primary object of the present invention is to obtain a novel effective method of treatment of PMS.

A primary object of the present invention is to obtain a readily available drug for the novel effective treatment of PMS.

Another object is to improve understanding of the mechanism and degree of benefits of a novel, effective method of treatment of PMS.

Another object is to obtain a simply administered novel, low-cost, effective method of treatment of PMS.

Another object is to make readily available to sufferers of PMS an improved method of treatment of PMS.

Another object is to obtain a novel method of treatment inclusive of preferred steps thereof that achieve maximum relief from PMS.

Another object is to establish a basis for use of a new class of drugs that could substantially improve the treatment of PMS.

Another object of this invention is to improve understanding and appreciation of the mechanism(s) involved in the human body of a women patient by which the present novel method of relief of PMS is operative and effective to a maximum degree.

Other objects become apparent from the preceding and following disclosure.

BROAD DESCRIPTION OF THE INVENTION

This invention is broadly directed to a treatment for moderating and/or blocking and/or obviating and/or eliminating premenstrual syndrome by the blocking of AT1 receptors in the subfornical organ (SFO), organum vasculosum of the lamina terminalis (OVLT), median preoptic nucleus, nucleus of the solitary tract, ventral hippocampus, area postrema of the hypothalamus and other areas of the hypothalamus on an interim basis during the luteal phase of a menstrual cycle of a patient suffering from premenstrual syndrome characterized by a concurrent plurality of symptoms inclusive of one or more affective and/or autonomic and/or somatic PMS symptoms of substantially incapacitating severity prior to the menses. Such syndrome is characterized by the plurality of symptoms being cumulatively of an incapacitating severity. The foregoing method embodies the intermittent administering of a drug already in existence and known as an angiotensin II subtype 1 receptor antagonist (AT1). The drug normally may be administered either orally or parenterally continuously to a female during her menstrual cycle's luteal phase normally heretofore characterized to her as being accompanied by premenstrual syndrome characterized by one or more indications such as physical, psychological and behavioral symptoms of substantially incapacitating severity(ies) proximately substantially prior to menses of a menstrual cycle. The choice of whether parental or oral dosage is employed, largely depends upon the preference of the doctor and/or patient, reflective of the total number and/or severity of the PMS symptoms present, the parental administration achieving relief more rapidly. It is also possible to effectively utilize time-release and/or delayed release tablets or capsules of the general types and mechanisms already conventionally available and applied to numerous various drugs of different types an functions in the market already, which technology is readily adaptable to the making of such tablets.

More particularly, the aforestated novel method of moderating premenstrual syndrome includes the following step(s). The method includes administering substantially continuously at-least one AT1 antagonist during each of recurring intermittent PMS symptomatic time periods corresponding to repetitively occurring symptoms substantially characterized by premenstrual symptoms corresponding and repetitively occurring in the luteal phase of the menstrual cycle. The AT1 antagonist is/are administered to a female having menstrual cycle(s) characterized during at least the luteal phase thereof by premenstrual syndrome inclusive normally of a plurality of at least one typically at least two of affective and/or autonomic and/or somatic symptoms that are one or more singly or at-least cumulatively of substantially incapacitating severity at point(s) in time substantially prior and proximate to menses of a menstrual cycle. The AT1 antagonist inhibit(s) the activity of at-least one type of ovarian hormone regulated receptor by blocking the binding of Ang II available to stimulate said AT1 receptors. The method's administering includes treating the patient by at least one oral or parenteral administration of the AT1 antagonist.

A first preferred method includes initiating the administering to the female substantially predominately during at least substantially the luteal phase of a menstrual cycle that is substantially subsequent to a follicular phase that is substantially prior to a next-occurring menses phase of a menstrual cycle and terminating the administration substantially at a beginning of a next-occurring menses phase.

In a second preferred embodiment, the administering is a at least by oral administration of the AT1 antagonist.

In a third preferred embodiment as an alternate to the aforestated first preferred invention the administration further includes parenterally administering the AT1 antagonist to the female, as necessary.

In a fourth preferred embodiment as an alternate improvement on the aforestated broad invention, the administering includes administering at least one of the following (identified by their Clinical Code Name, followed by their chemical name if known, and the Company undertaking their development): Losartan (DUP-753), having the chemical name 2-n-butyl-4-chloro-5-hydroxymethyl-1-[2( 1H-tetrazol-5-yl)biphanyl-4-yl-methyl]imidazole-[CAS], under development by DuPont Merck; DUP-532, having the chemical name (1H-imidazole- 5-carboxylic acid, 4-(pentafluoroethyl)-2-propyl- 1-[[2'-(1H-tetrazol-5yl)[1,1'-biphenyl]- 4-yl]methyl]), under development by DuPont Merck; BIBR-277, having the chemical name (4'[( 1,4'-dimethyl-2'-propyl [2-b'-bi-1h-benzimidazol]-1'-yl)methyl]-[1,1'- biphenyl]-2-carboxylic acid, under development by Boehringer Ingelheim; RWJ-38970, chemical name unknown (a substituted 3-mercaptotriazole angiotensin II receptor angtagonist), under development by Johnson & Johnson; RWJ-46458, having the chemical name (2-carbethoxymethylidene-4-methyl-4-ethyl- 2-[4-(2'-tetrazolo)-phenyl]benzylpiperidin-6-one) under development by Johnson & Johnson; YM-358, having the chemical name (2,7-diethyl-5-[[2'-(5-tetrazolyl)biphenyl- 4-yl]methyl]-5H-pyrazolo[1,5-b][1,2,4]triazole), under development by Yamanouchi; ZD-7155, having the chemical name (5,7-diethyl- 1-[2'-(1H-1,2,3,4-tetrazol-5-yl)biphenyl-4-ylmethyl] -1,2,3,4-tetrahydro-1,6-naphthyridin-2-one HCl), under development by Zeneca; L-159878, chemical name unknown, under development by Merck & Co.; L-158809, chemical name unknown, under development by Merck & Co.; SC-51316, chemical name unknown, under development by Monsanto; SC-51895, chemical name unknown, under development by Monsanto; SK&F-108566, having the chemical name (3-[2-butyl-1-(4-carboxybenzyl)-1H-imidazol- 5-yl]-2-(2-thienylmethyl)-2-(E)-propenoic acid), under development by Smith Kline Beecham; UP269-6, chemical name unknown (an angiotensin II-1 (A-II-1) antagonist), under development by UPSA; CGP-48933, having the chemical name ((S)-N-valeryl-N-([ 2'-(1H-tetrazol-5-yl)biphenyl-4-yl]methyl)-valine), under development by Ciba-Geigy; CGP-48369, chemical name unknown (an angiotensin II antagonist), under development by Ciba-Geigy; WAY-126227, chemical name unknown (a nonpeptide angiotensin II (AII) receptor antagonist), under development by American Home Products; ZD-8731, chemical name unknown, under development by Zeneca; KT3-671, chemical name unknown (an angiotensin II (AII) antagonist), under development by Kotobuki-Seryaku; and SR-47436, having the chemical name (2-n-butyl-4-spirocyclopentane -1-[((2'-tetrazol-5-yl)biphenyl-4-yl)methyl]-2-imidazolin-5-one), under development by Elf Sanofi.

All of the above are antagonists directed at the AT1 receptor, but the scope of the invention includes compounds (i.e. salts) derived from the above by reactions with various organic and inorganic acids and bases. Such salts include ammonium salts, alkali metal salts (eg. sodium, potassium), alkaline earth metal salts (eg. calcium, magnesium), salts with organic bases (eg. dicyclohexylanine, N-methyl-D-glucamine), and salts with amino acids such as lysine, arginine and the like. Also, salts of inorganic acids may be prepared (eg. HCl, $H_3PO_4$, malic, fumaric). The non-toxic physiologically acceptable salts are preferred.

The compounds of this invention can be administered to patients needing treatment in compositions such as tablets, capsules, elixirs for oral administration, suppositories for rectal administration, sterile solutions or suspensions for parenteral, intramuscular or intravenous use in dosages that will provide optimal pharmaceutical efficacy. The dose may vary from patient to patient depending on the patients weight, diet, concurrent medication or illnesses and severity of the disorder. The dosage will be from 0.5 mg to 500 mg per day per patient, administered in a single dose or in multiple doses. A further embodiment of the invention as an improvement on the previous embodiment is to administer the compounds of this invention in combination with (low doses) of diuretics such as hydrochlorothiazide, chlorthalidone or chlorthiazide and/or with angiotensin converting enzyme inhibitors such as lisinopril, enalapril, quinapril, ramipril captopril, zopenopril, fosinopril, trandolapril, and perindopril. The addition of one of the abovementioned agents to the AT1 antagonist should increase the rapidity or/and the completeness of therapeutic response in a percentage of patients. To illustrate these combinations, the AT1 antagonist can be combined as follows for a daily dose range: (1) hydrochlorothiazide (6.25–12.5 mg), chlorthiazide (60 mg–125 mg); quinipril ( 1.25 mg)–5 mg), enalapril (0.25 mg–2.5 mg), lisinopril (5 mg–10 mg) or chlorthaladine (6.25 mg–12.5 mg).

In a fifth preferred embodiment as an alternate improvement on the aforestated broad invention, the administering includes administering at-least one AT1 antagonist at at an oral dosage ranging from about 0.5 mg to about 500 mg over a period of substantially twenty-four hours, during a luteal phase of the female menstrual cycle.

In a further alternate sixth preferred embodiment as an improvement on the first preferred embodiment, the administering includes the same improvement as the fourth preferred embodiment.

In a further seventh preferred embodiment as an improvement on the fourth preferred embodiment, the administration further includes the same improvement as the second preferred embodiment.

In a further alternate eighth preferred embodiment as an improvement on the fourth preferred embodiment, the administration includes the same improvement as the third preferred embodiment.

In a further ninth preferred alternate embodiment as an improvement on the fourth preferred embodiment, the method is the same as the fifth preferred embodiment.

In a further tenth preferred embodiment as an alternate improvement on the aforestated broad invention, the administering includes administration of losartan as the AT1 antagonist substantially during a luteal phase of a menstrual cycle subsequent to a follicular phase.

The eleventh embodiment established by prior art includes the use of any of a group of valid questionnaires, visual analog scales representations of premenstrual symptom intensity or other instruments recording said data reflecting a plurality of menstrual cycles and thereafter subsequent to said recording administering an AT1 antagonist to at least one selected patient having said PMS symptoms. Administration can be oral or parenteral with oral the preferred route and taking the dose once twice or three times daily substantially during the luteal phase of their menstrual cycle and at or immediately after the onset of the menses phase. This is repeated each month as required. The dose of each AT1 antagonist should be from 0.5 mg to 500 mg daily and should be a dose shown by prior art to be within the range of doses employed for human use.

The invention may be better understood by making reference to the following drawings and tables of the Figures.

DETAILED DESCRIPTION

Figure 1:
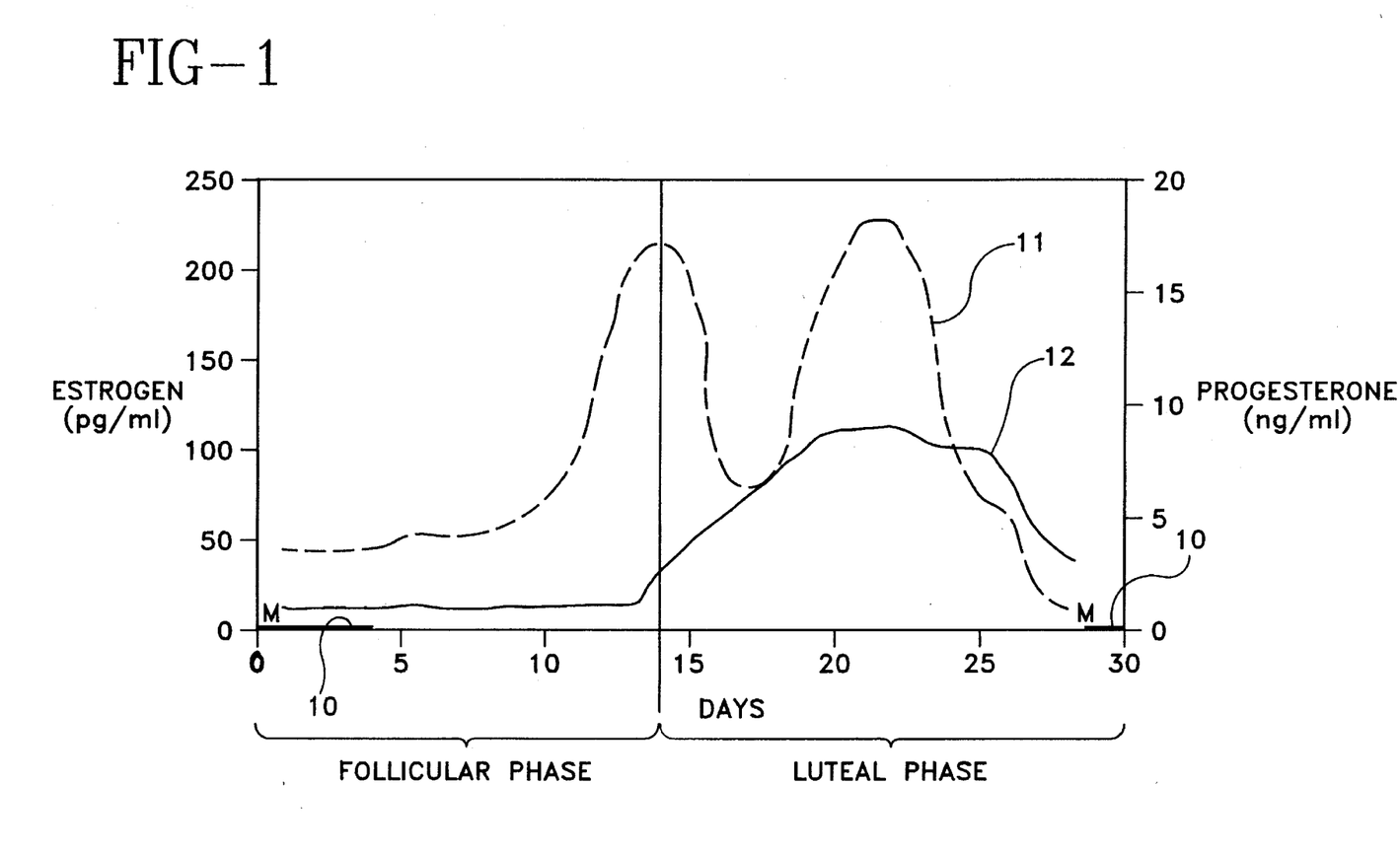
FIG. 1 illustrates the hormonal changes occurring during the human menstrual cycle.
Figure 2:
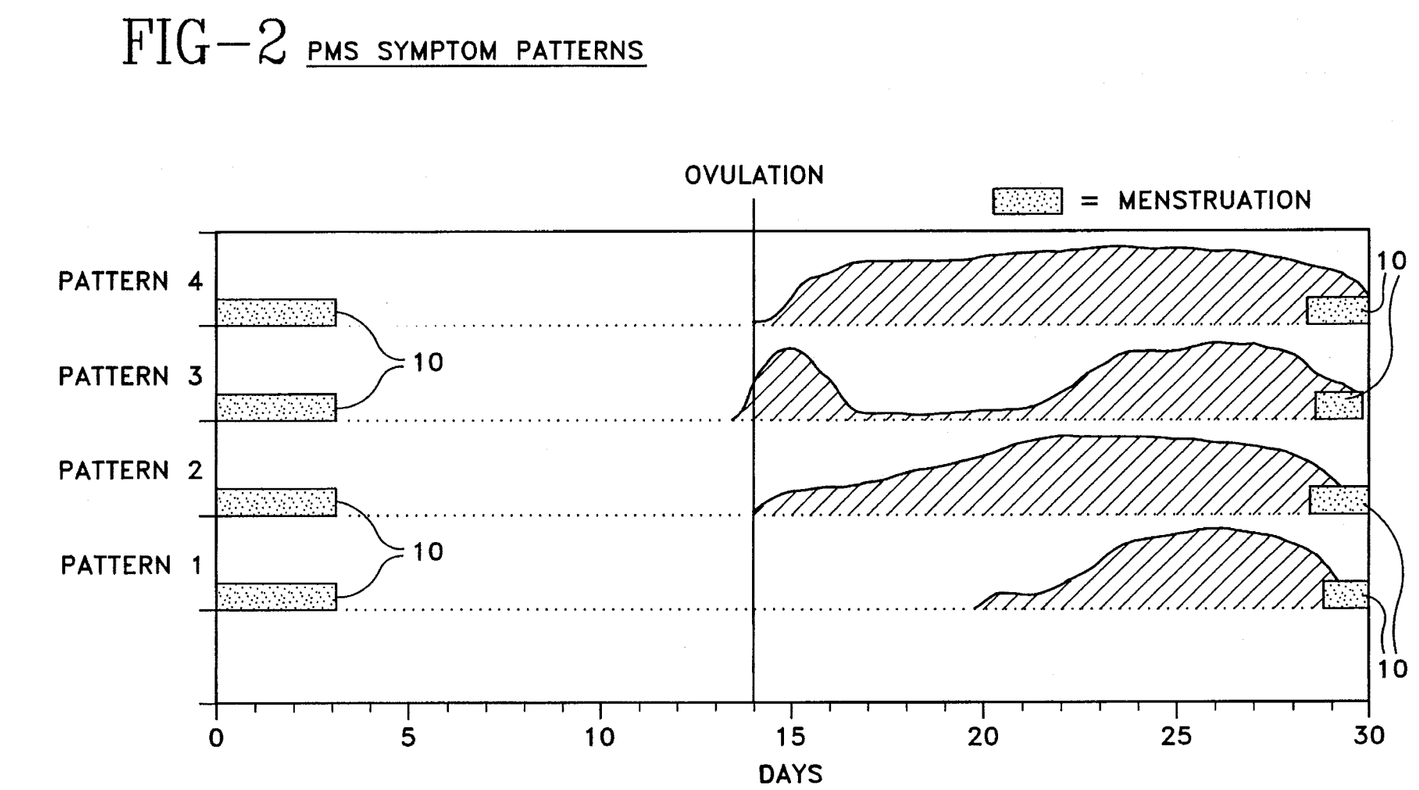
FIG. 2 depicts the patterns of PMS symptoms experienced by patients.
Figure 3:
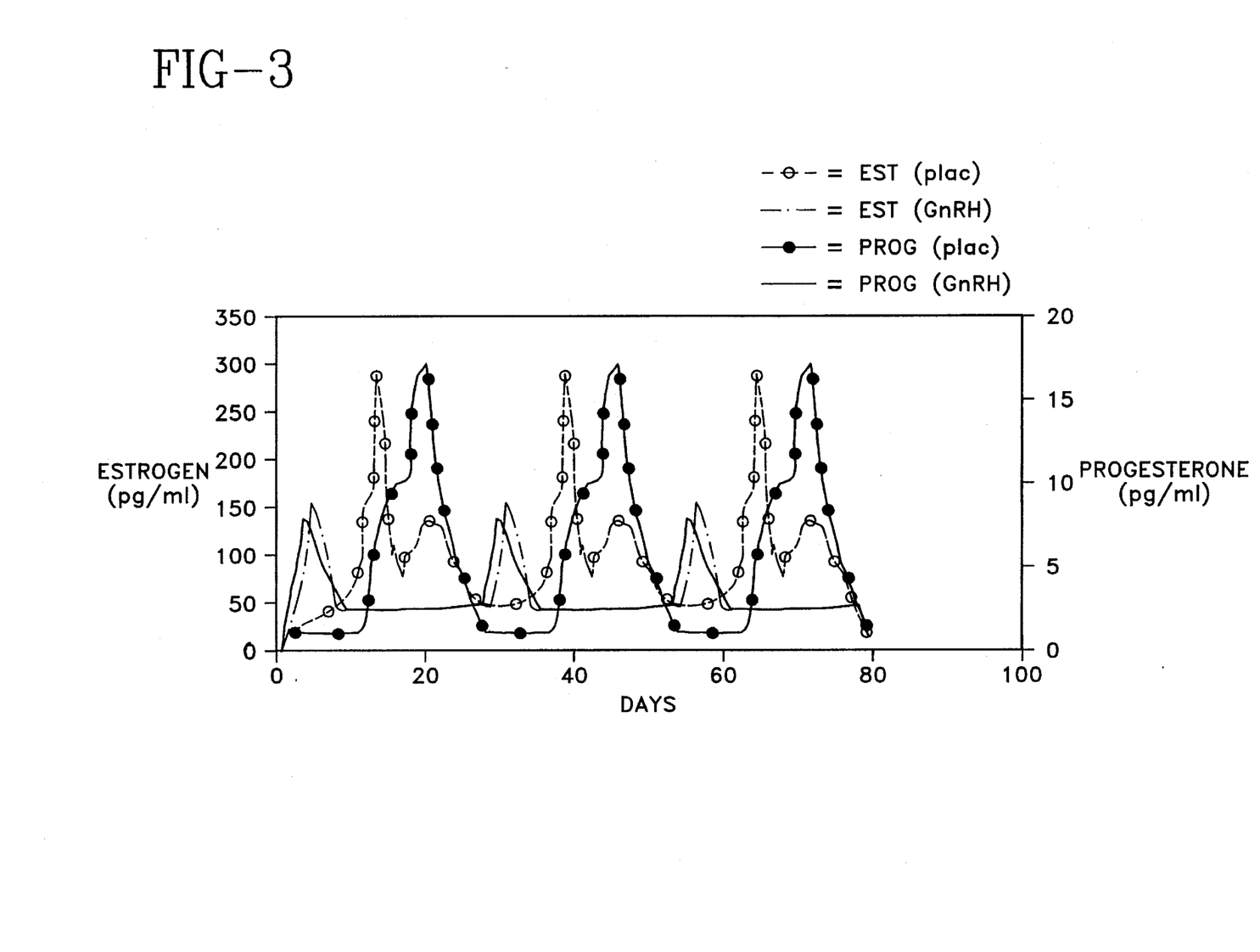
FIG. 3 shows the effect of daily injections of a GnRH agonist on circulating levels of ovarian hormones compared to placebo-treated patients.
Figure 4:
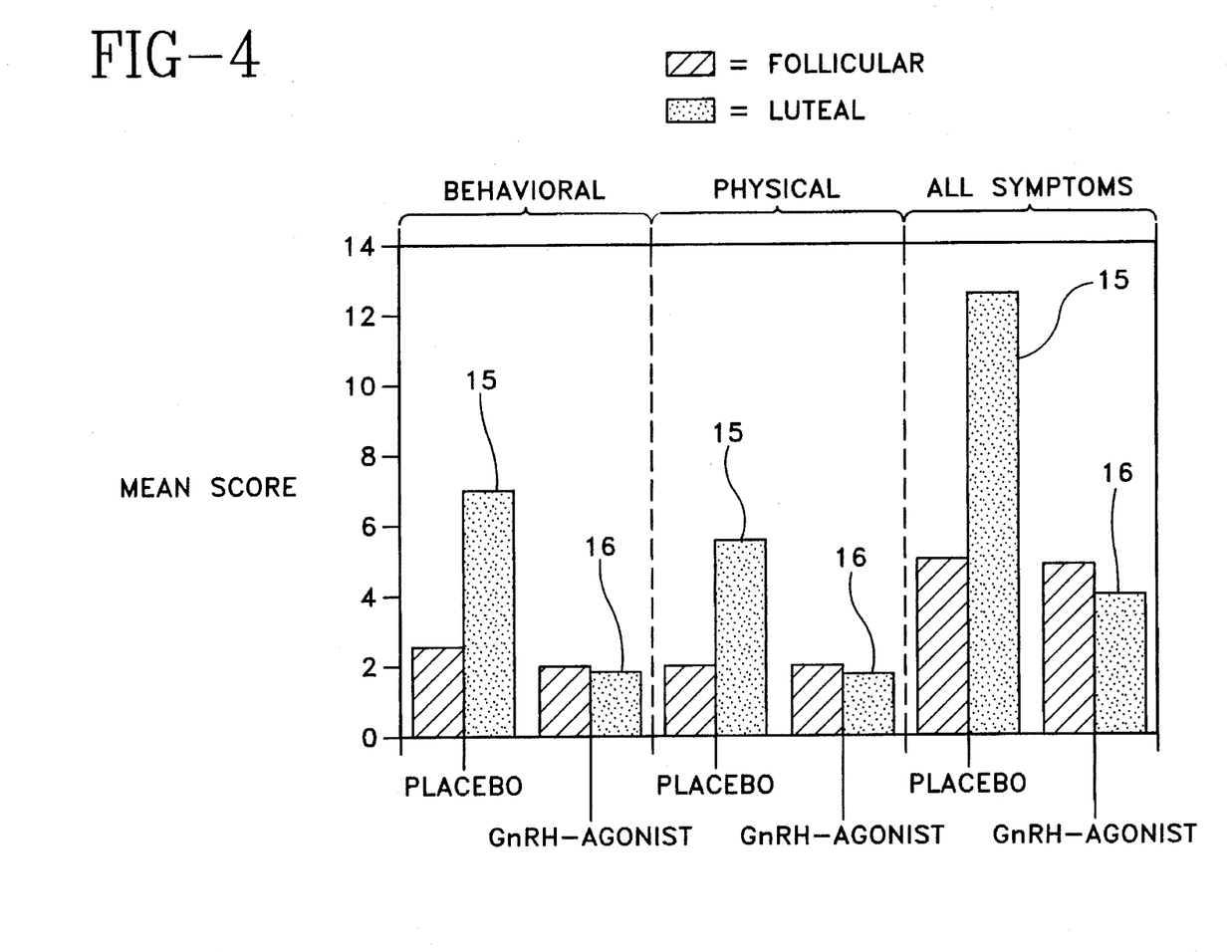
FIG. 4 the effect of daily injections GnRH agonist in the same patients as FIG. 3, but relates the effects to the severity of premenstrual symptoms.

The menstrual cycle of the human female is divided into follicular and luteal phases. FIG. 1 shows the hormonal changes that occur during the menstrual cycle. Days 1 through 5 are the days of the menses and correspond to the time when the menstrual flow is occurring. This period is sometimes referred to as the menstrual phase (indicated by the letter M 10). Premenstrual Syndrome (PMS) is the cyclic recurrence in the luteal phase of a combination of physical, psychological and/or behavioral symptoms which significantly impair social or occupational functioning. Most women experience symptoms for 1 to 14 days usually beginning after ovulation which occurs approximately on Day 14. FIG. 2 shows several symptom patterns reported by patients who suffer from PMS. Referring to FIG. 1, the symptom periods correspond with a time when there are high levels of both estrogen 11 and progesterone 12. The symptoms usually remit with the onset of menses or within a few days afterwards. Also, as seen in FIG. 1, this period is when levels of estrogen and progesterone are lowest. Ninety percent (90%) of menstruating females exhibit some symptoms of PMS, but only 20–40% of patients are incapacitated to some degree and require therapy. No previous study has uncovered the link between the cyclic changes in the hypothalamic-pituitary-ovarian axis and the myriad of symptoms of PMS (1–3). (Anderson, M. et al., *Premenstrual syndrome research: Using the NIMH guidelines*, J. Clin. Psychiatry 49:484–86, 1988. York, R., et al.; *Characteristics of premenstrual syndrome*, Obstet and Gynecol., 73(4):601–605, 1989. Smith, S.; Schiff, I., *The premenstrual syndrome—diagnosis and management*, Fertility and Sterility, Vol. 52, No. 4, October 1989.). Since the syndrome is related to the ovarian cycle, there would appear to be a causal relationship to either estrogen, progesterone and/or some ratio of estrogen and progesterone. Three studies have clearly shown the role of ovarian hormones. Muse, et. al, (4) (Muse, K. N.; Cetel, N. S., Futterman, L. A.; Yen, S. S. C., *The premenstrual syndrome: effects of "medical ovariectomy"*, N Engl J Med 311:1,345, 1984) demonstrated that medical ovariectomy by daily injections of a GnRH agonist reduced the cyclic hormonal changes of estrogen (E2) 13 and progesterone (P4) 14 as seen in FIG. 3. In FIG. 3, patients with moderate to severe PMS were treated with placebo or GnRH agonist for three months and measurements of hormone levels were made in the same patients during each course of therapy. The fluctuations in ovarian hormones were abolished when compared to placebo-treated patients. FIG. 4 shows, in the same patients, the effects of reducing ovarian hormones on premenstrual symptoms. In FIG. 4, the typical physical and behavioral symptoms occur during the luteal phase 15 with placebo treatment but are significantly reduced (P<0.05) when the patients are treated with the GnRH agonist 16. In a second study by Casper, et al, (5) (Casper, R. F.; and Hearn, M. T.; *The effect of hysterectomy and bilateral oophorectomy in women with severe premenstrual syndrome*, Am. J. Obstet. Gynecol 162:105–9; 1990.) a series of patients underwent surgical ovariectomy and showed complete resolution of their symptoms. Finally, Hammarback, et al, (6) (Hammarback, S.; Backstrom, T.; Hoist, J.; von Schoultz, B.; Lyrenas, S.: *Cyclical mood changes as in the premenstrual tension syndrome during sequential estrogen.:progestogen postmenopausal replacement therapy*. Acta Obstet Gynecol. Scand 64:393, 1985.) reported cyclical mood changes in postmenopausal patients receiving sequential estrogen and progesterone replacement therapy. Together these data clearly demonstrate the pivotal role of ovarian hormones in the genesis of PMS.

Despite these observations, numerous controlled studies that have tried to treat PMS by utilizing progesterone, oral contraceptives or synthetic androgens have shown minimal success, with relief of some symptoms but frequent undesirable side effects. In many studies these therapies were often not distinguishable from placebo therapy (3,7–14) (Smith, S.; Schiff, I., *The premenstrual Syndrome—diagnosis and management*, Fertility and Sterility, Vol. 52, No. 4, October 1989. Maddock, S.; Hahn, P.; Moller, F.; Reid, R. L.; *A double-blind placebo-controlled trial of progesterone vaginal suppositories in the treatment of premenstrual syndrome*, Am. J. Obstet. Gynecol. 154(3):573–81, March, 1986. Dennerstein, L.; Spencer-Gardner, C.; Gotts, G.; Brown, J. B.; Smith, M. A.; Burrows, G. D.; *Progesterone and premenstrual syndrome: a double-blind crossover trial*, Br. Med. J. 290:1,617, 1985. Sampson, G. A.; *Premenstrual syndrome: A double-blind controlled trial of progesterone and placebo*, Br. J. Psychiatry 135:209, 1979. Sampson, G. A.; Heathcote, R. P.; Wordsworth, J.; Prescrott, P.; Hodgson, A.; *Premenstrual syndrome: A double-blind cross-over study of treatment with dydrogesterone and placebo*, Br. J. Psychiatry, 153:232–5, 1988. Walker, A.; Bancroft, J.; *Relationship between premenstrual symptoms and oral contraceptive use: a controlled study*, Psychosom. Med. 52(1):86–96, January-February, 1990. Silberfeld, S.; Brast, N.; Noble, E. P.; *The menstrual cycle: a double-blind study of symptoms, mood and behavior and biochemical variables using Enovid and placebo*, Psychosom. Med. 33:411, 1971. Watts, J. F.; Butt, W. R.; Edward, R. L.; *A clinical trial using danazol for the treatment of premenstrual tension*, Br. J. Obstet. Gynaecol. 94:30, 1987. Andersen, A. N.; Streenstrup, O. R.; Svendstrup, B.; Nielsen, J.; *Effect of bromocryptine on the premenstrual syndrome: a double-blind clinical trial*, B. J. Obstet. Gynaecol. 84:370, 1977.) All of this has raised questions about the mechanism by which ovarian hormones produce these effects. Also, there are no studies that link the cyclic hypothalamic-pituitary-ovarian changes with any endocrine abnormality which might explain PMS.

The relationship of the renin-angiotensin aldosterone (RAA) system to fluid and salt balance is well known; however, there is also a correlation between increasing levels of progesterone in the luteal phase of the menstrual cycle with increasing aldosterone and Angiotensin II (Ang II) (17) (Sundsfiord, J. A.; Aakvaag, A.; *Plasma angiotensin II and aldosterone excretion during the menstrual cycle*, ACTA Endocrinologica 64, 452–58, 1970.) Janowsky, et al, (18) (Janowsky, D. S., et al.; *Correlations between mood, weight, and electrolytes during the menstrual cycle: A renin angiotensin hypothesis of premenstrual tension*, J. Psychosom. Med.; 35:143–154, 1973.), hypothesized that Ang II and aldosterone might be factors in the cause of PMS. However, no studies have subsequently demonstrated any relationship of the circulating levels of ovarian hormones, aldosterone or Ang II to the occurrence of PMS.

The following facts lead to the hypothesis that AT1 receptors are key modulators of premenstrual symptoms:

1. Ovarian hormones are necessary for the genesis of PMS
2. Ovarian hormones modulate AT1 receptor density and function, and The location and function of AT1 receptors in the hypothalamus and central nervous system suggests they can be mediators in producing the symptoms of PMS(19–23) (Unger, T.; Badoer, E.; Ganten, D.; Lang, R.; Rettig, R.; *Brain angiotensin: pathways and pharmacology*, Circulation 77 (suppl 1), 1–40, 1988. Ganong, W. F.; *Angiotensin II in the brain and pituitary: Contrasting roles in the regulation of adenohypophyseal secretion*, Horm. Res. 31:24–31, 1989. Jhamandas, J. H.; Lind, R. W.; Renaud, L. P.; *Angiotensin II may mediate excitatory neurotransmission from the subfornical organ to the hypothalamic supraoptic nucleus: an anatomical and electrophysiological study in the rat*, Brain Research, 487:52–61, 1989. Kadekaro, M.; Cohen, S.; Terrell, M. L.; Lekan, H.; Gary, H.; Eisenberg, H.; *Independent activation of subfornical organ and hypothalamoneurohypophysial system during administration of angiotensin II*, Peptides, Vol. 10, pp 423–429, 1989. Scholkens, B. A.; Jung, W.; Rascher, W.; Dietz, R.; Ganten, D.; *Intracerebroventricular angiotensin increases arterial blood pressure in rhesus monkeys by stimulation of pituitary hormones and the sympathetic nervous system*, Experientia 38:469, 1982.) The first point was discussed previously.

Figure 5:
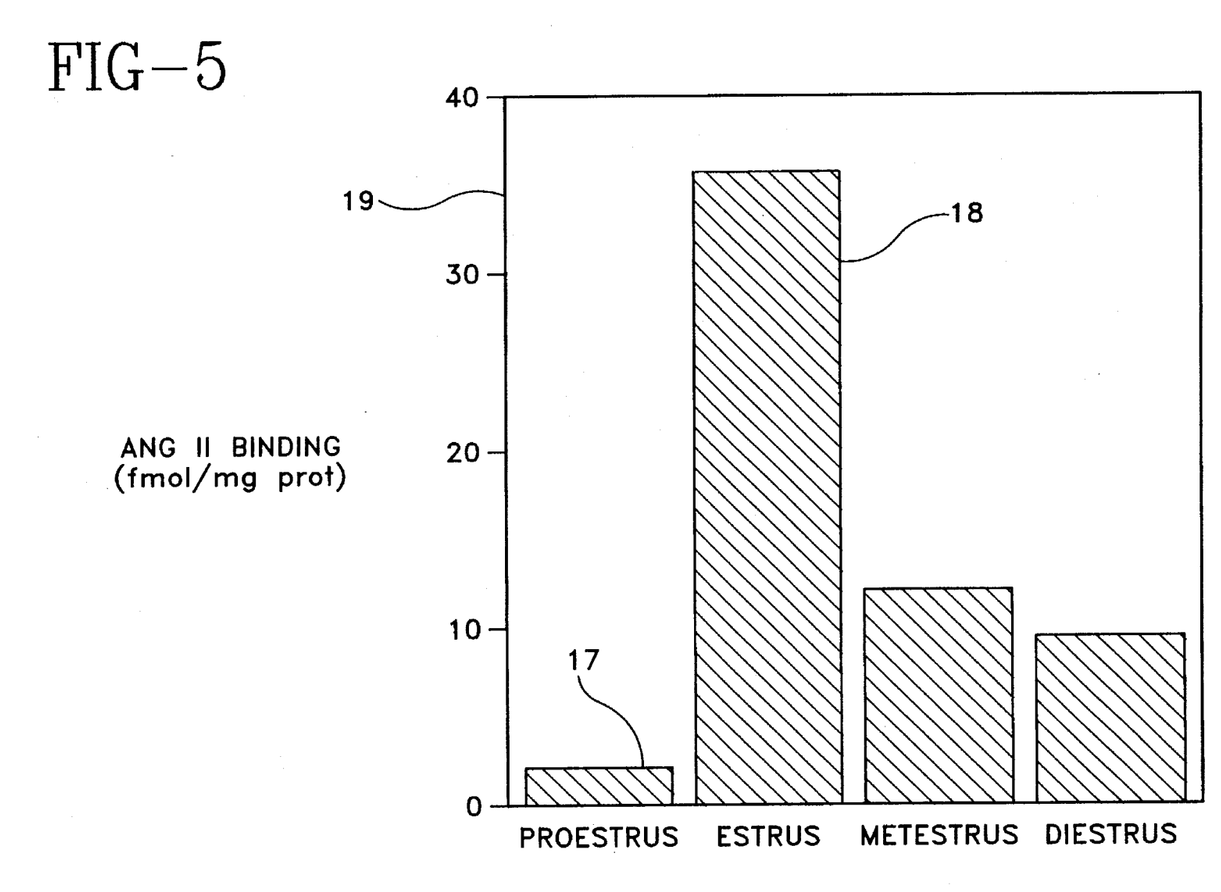
FIG. 5 shows the effect of cyclic ovarian hormones changes in the rat on the number of AT1 receptors identified.
Figure 6:
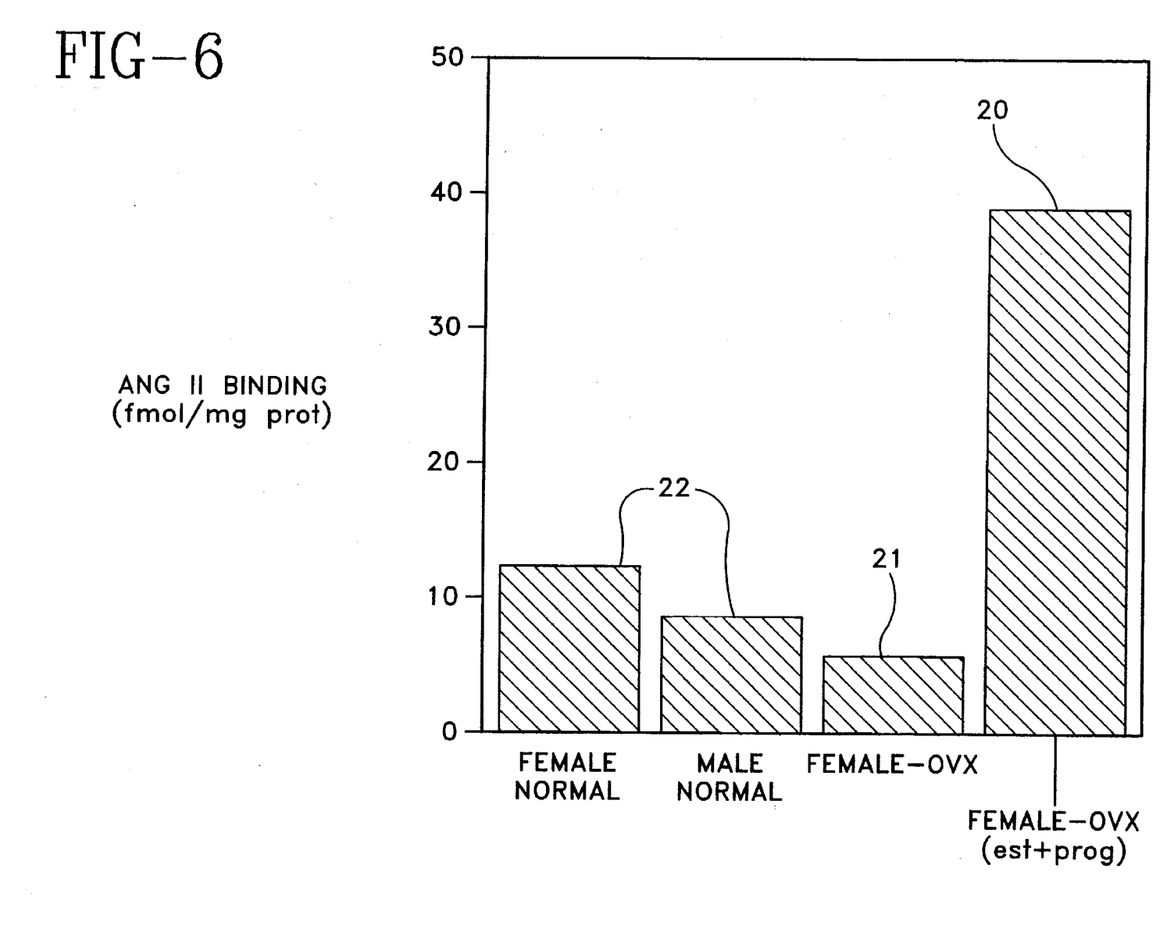
FIG. 6 shows the comparisons between the normal number of AT1 receptors in male and female rats compared to rats which have been ovariectomized and subsequently treated with estrogen and progesterone.

The AT1 receptor is known to mediate the potent constrictor effects on smooth muscle (i.e. vascular), the release of aldosterone from the adrenal cortex and centrally activates or facilitates the activity of the sympathetic nervous system (19-26) (Unger, T.; Badoer, E.; Ganten, D.; Lang, R.; Rettig, R.; *Brain angiotensin: pathways and pharmacology*, Circulation 77 (suppl 1), 1–40, 1988. Ganong, W. F.; *Angiotensin II in the brain and pituitary: Contrasting roles in the regulation of adenohypophyseal secretion*, Horm. Res. 31:24–31, 1989. Jhamandas, J. H.; Lind, R. W.; Renaud, L. P.; *Angiotensin II may mediate excitatory neurotransmission from the subfornical organ to the hypothalamic supraoptic nucleus: an anatomical and electrophysiological study in the rat*, Brain Research, 487:52–61, 1989. Kadekaro, M.; Cohen, S.; Terrell, M. L.; Lekan, H.; Gary, H.; Eisenberg, H.; *Independent activation of subfornical organ and hypothalamo-neurohypophysial system during administration of angiotensin II*, Peptides, Vol. 10, pp 423–429, 1989. Scholkens, B. A.; Jung, W.; Rascher, W.; Dietz, R.; Ganten, D.; *Intracerebroventricular angiotensin increases arterial blood pressure in rhesus monkeys by stimulation of pituitary hormones and the sympathetic nervous system*, Experientia 38:469, 1982. Shigeru, O.; Kiyotoshi, I.; Toshio, K.; and Hiroshi, Y.; *Angiotensin II sensitive neurons in the supraoptic nucleus, subfornical organ and anteroventral third ventricle of rats in vitro*, Brain Res. 402:58–67, 1987. Speth, R. C.; Grove, K. L.; and Rowe, B. P.; *Angiotensin II and the locus coeruleus*, Progress in Brain Res. 88:217–223, 1991. Speth, R. C.; Wamsley, J. K.; Gehlert, D. R.; Chernicky, C. L.; Barnes, K. L.; and Ferrario, C. M.; *Angiotensin II Receptor Localization in the Canine CNS*, Brain Res 326:137–143, 1985.) How the AT1 receptor mediates Ang functions is uncertain, but the distribution is different in various organs and tissues (27) (Catt, K. J.; Mendelsohn, F. A.; Millan, M. A.; and Aguilera, G.; *The role of angiotensin II receptors in vascular regulation*, J. Cardiovasc. Pharmacol., 6 (Suppl 4) S575–S586, 1984.) It seems probable that ovarian hormones regulate Ang II receptor activity by altering their density, or binding characteristics. To demonstrate this Grove, et al, (28) (Grove, K. L.; Speth, R. C.; Sylvester, P. W.; Brisk, K. P.; *Gonadal steroids alter brain angiotensin II receptors in ovariectomized rats*, Soc. for Neuroscience Abstracts, V:18, p1162, 1992.) administered to rats estrogen and progesterone after ovariectomy. Compared to non-treated rats, they had an increase in the number of Ang II receptors in the hypothalamic nuclei. Phillips, et al, (29) (Phillips, M. I. et al.; *Dynamic changes in hypothalamic angiotensin II levels and release in association with the progesterone induced LH surge*, Endocrinol V132, pp 1637–42, 1993) confirmed an increase in hypothalamic Ang II levels and release in association with the estrogen/progesterone induced LH surge. These animals were ovariectomized but only those pretreated with ovarian hormones responded. Finally Seltzer, (30) (Seltzer, A., et al.; *Reproductive hormones modulate angiotensin II receptors in the dorsomedial arcuate nucleus of the female rat*, Endrocrinol V133, pp939–941, 1993.) recently showed that the number of AT1 receptors in the dorsomedial arcuate nucleus of the hypothalamus of the rat is low at proestrus (low estrogen) 17 and increases significantly at estrus (high estrogen) 18 (FIG. 5). In FIG. 5 the period of estrus 18 corresponds to the luteal phase of the human menstrual cycle when there are high levels of estrogen and progesterone. This figure illustrates how the changing levels of estrogen and progesterone can alter the number of Ang receptors 19. This was confirmed when animals were ovariectomized then treated with exogenous estrogen and progesterone 20 and showed a similar increase in AT1 receptors, while non-treated animals showed no increase 21 (FIG. 6). Measurements of Ang II receptors were also made in normal male and female rats 22 and the results compared to the rats which were subjected to an ovariectomy (OVX) 20. FIG. 6 shows that the number of AT1 receptors in the group which received the ovarian hormones showed a five-fold increase ($P<0.05$).

Speth, et al, (31) (Speth, R. C.; Wright, J. W.; and Harding, J. W.; *Brain angiotensin receptors: Comparison of location and function.* In J. W. Harding, J. W. Wright, R. C. Speth and C. D. Barnes (Eds.), *Angiotensin and Blood Pressure Regulation*, Academic Press, New York, N.Y., pp 1–34, 1988. ) reviewed the functions of AT1 in the central nervous system (CNS). Within the CNS, Ang II also serves as a neurotransmitter or neurohormone (32) (Sirett, N. E.; Hubbard, J. I.; Bray, J. J.; *Brain angiotensin II receptors*; Exp Brain Res. (Suppl 4), 233–241, 1982.). Therefore, neurons from various parts of the brain (eg. amygdala/hippocampus, which are involved in feeding behavior and emotional displays such as fear and rage) may contain few AT1 receptors but utilize Ang II as a neurotransmitter. These neurons may project to other areas of the brain (eg. hypothalamus) where receptors are present. Thus activation of these neurons releases Ang II which stimulates the AT1 receptors at a distant site. If the receptor density is increased, then the response to the same stimulus may vary. Thus, alteration of AT1 receptor density by ovarian hormones could alter the strength of response and this will vary as a function of the phase of the ovarian cycle. In addition, it may modify not only the strength of response but the type (i.e. inhibition verses stimulation).

In a review by Unger, et al, (19) (Unger, T.; Badoer, E.; Ganten, D.; Lang, R.; Rettig, R.; *Brain angiotensin: pathways and pharmacology*, Circulation 77 (suppl 1), 1–40, 1988.) the authors described areas of the brain which lie outside the blood brain barrier but are important Ang II pathways. These areas, the subfornical organ (SFO) and the organum vasculosum of the lamina terminalis (OVLT) are rich in AT1 receptors and converting enzyme and are stimulated by peripheral circulating as well as brain Ang II. Both have connections to the hippocampus and areas of the hypothalamus and thalamus. It may be through these pathways that Ang II is able to modulate blood pressure and influence the release of hypophysial hormones.

To explain how Ang II might mediate these effects, Steel and Ganong, (33–34) (Ganong, W. F.; *Angiotensin II in the brain and pituitary: Contrasting roles in the regulation of adenohypophyseal secretion*; Horm Res 31:24–31, 1989. Steele, M. K.; Ganong, W. F.; *Effects of catecholamine-depleting agents and receptor blockers on basal and angiotensin II-or norepinephrine-stimulated luteinizing hormone release in female rats*, Endocrinology, Vol. 119, No. 6, 1986.) showed that Ang II stimulates the release of norepinephrine (NE) in the preoptic area of the hypothalamus, and that this results in the release of LH. Gallo (35) (Gallo, R. V.; *Neuroendocrine regulation of pulsatile luteinizing hormone release in the rat*, Neuroendocrinology 30:122–131, 1980.), demonstrated that NE inhibited the release of LH when administered to ovariectomized rats; but this was converted to stimulation of LH release by replacement doses of estrogen and progesterone. This is an example of how the type of response might vary depending on the phase of the cycle.

All of these data clearly demonstrate the regulatory activity of ovarian hormones in modulating Ang II receptor functions in the hypothalamus. The hypothalamus is an important integrating center which is interconnected to many other areas of the central nervous system (CNS). The demonstrated variability of AT1 receptor function caused by hormonal changes can produce marked variability in the responses.

Figure 9:
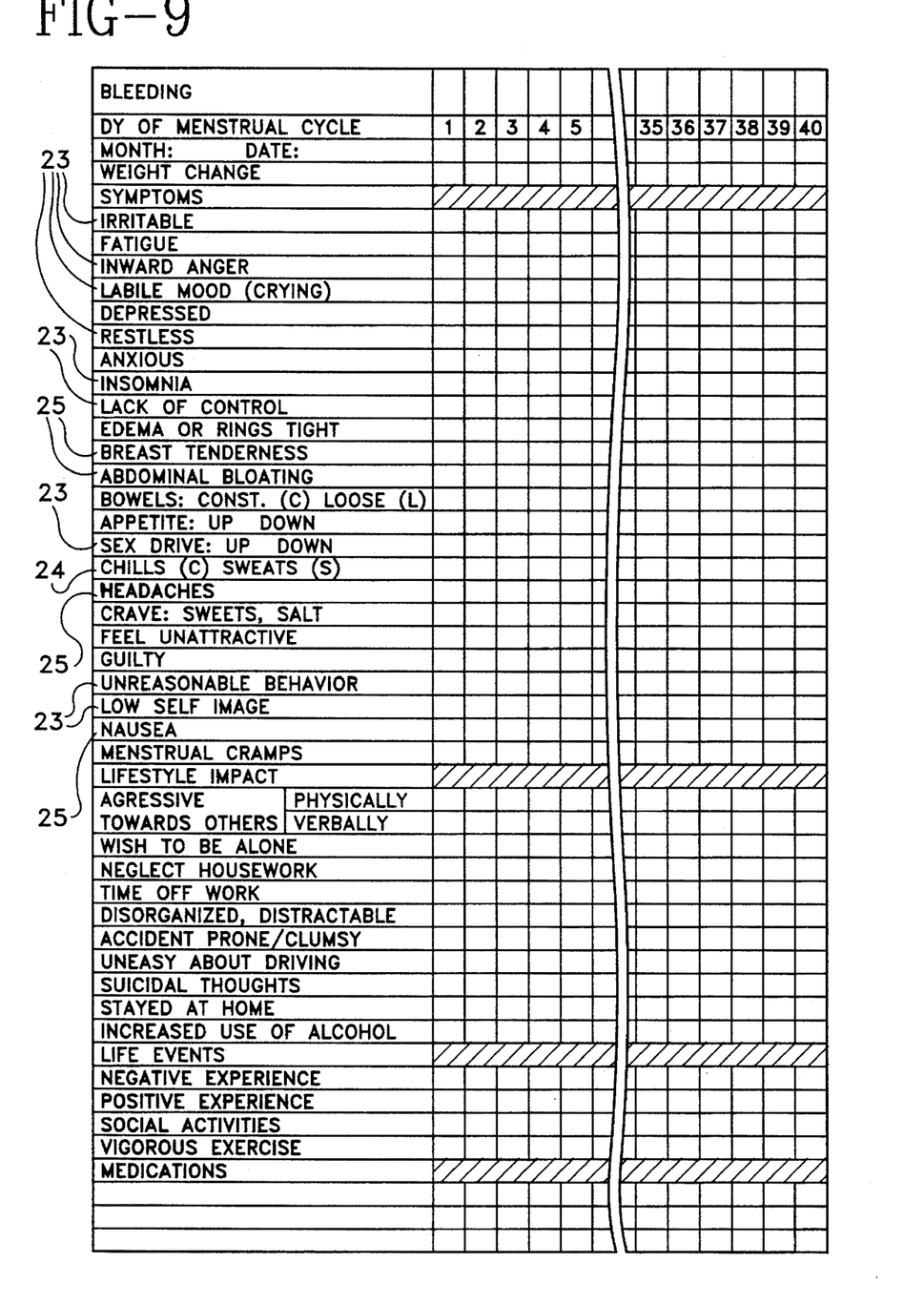
FIG. 9 shows an example of the PRISM symptom scoring sheet.

In order to link the previous anatomo-functional discussion with the symptoms of PMS, the PRISM calendar (Prospective Record of the Impact and Severity of Menstrual Symptoms, FIG. 9), is used clinically to document and evaluate the severity of PMS symptoms. From this calendar symptoms that cyclically appear can be grouped as follows:

1. Affective/Cognitive Symptoms 23:

Changes in libido, unreasonable erratic behavior, lack of emotional control, tension, mood swings, restlessness, insomnia, feelings of guilt, low self image, distractable, inward anger, lablie mood (i.e. crying) and/or irritability, and/or occasionally PMS-associated depression and/or anxiety.

2. Autonomic Symptoms 24:

Hot/cold flashes, palpitations, chills, sweating and dizziness

3. Somatic/Physical 25:

Edema, breast tenderness, bloating of the abdomen or extremities, nausea, headaches, pelvic or abdominal pain and fatigue.

Figure 7:
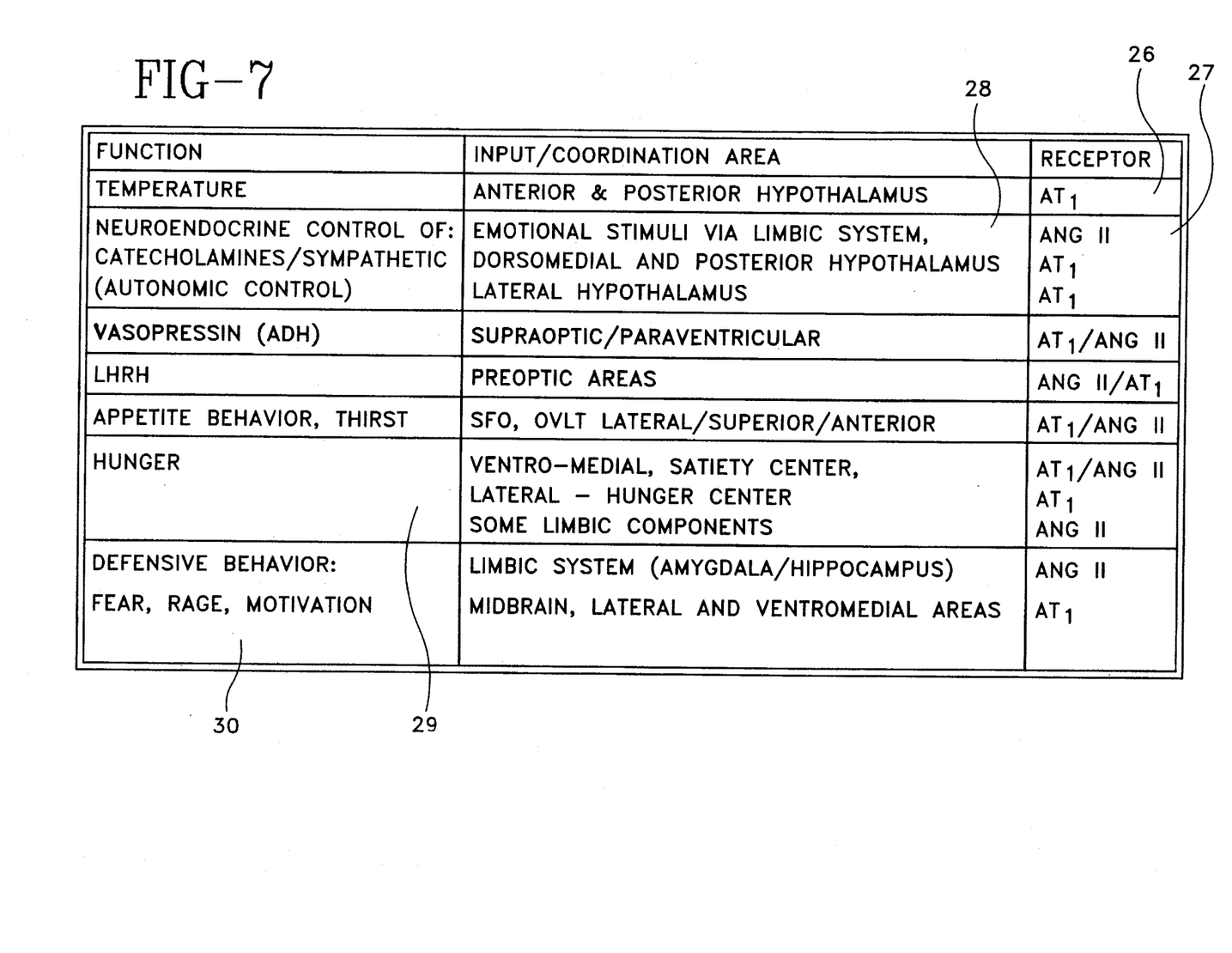
FIG. 7 depicts the anatomical areas of the hypothalamus, their various functions and the presence of AT1 receptors or Ang II.
Figure 8:
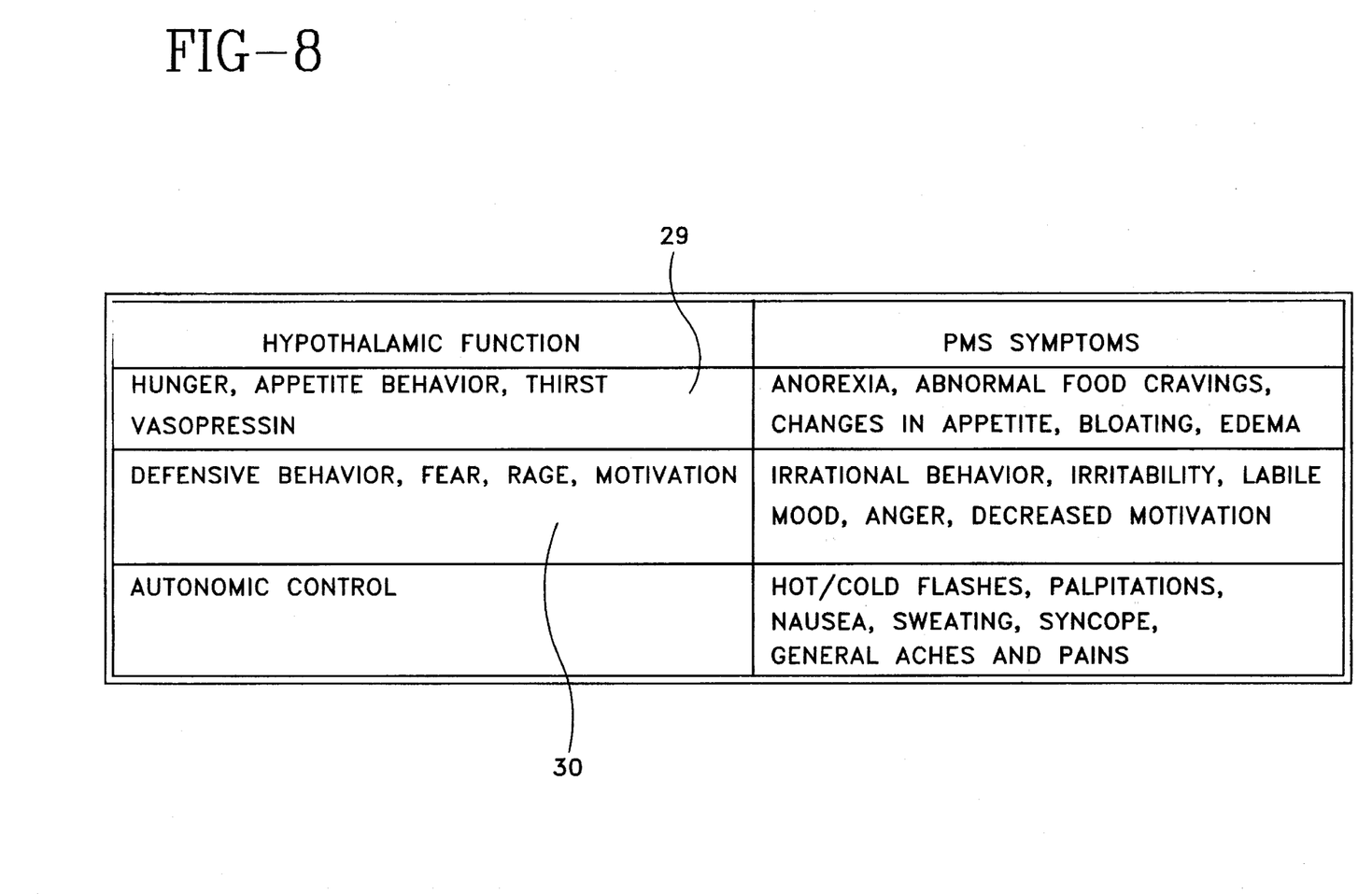
FIG. 8 relates the different PMS symptoms to hypothalamic areas known to modulate these symptoms or physiological effects.

First, in FIG. 7, the known functional aspects of the subdivisions of the hypothalamus are presented and its afferents are described (36) (Ganong, W. R.; *Review of Medical Physiology*, Appleton and Lange, 1987.). These anatomic loci contain Ang receptors and/or Ang II. "AT1" 26 designates the presence of AT1 receptors while "Ang II" 27 represents the presence of Ang II substance. The hypothalamus controls complex, emotional and behavioral reactions. It responds to various stimuli and serves to integrate these into an appropriate response. Stimulation of lateral areas can cause a rise in blood pressure usually in response to emotional stimuli 28. The middorsal portion can cause a dilation of blood vessels in the muscles and a constriction in the skin. The dorsomedial part can increase secretion of norepinephrine and epinephrine (adrenalin). These hormones increase sweating, heat rate and blood pressure. Stimulating the lateral part or "feeding center" increases eating, while damage to this causes severe anorexia 29. The ventromedial "satiety" center causes a cessation of eating when stimulated, but if the area is damaged, overeating or hypothalamic obesity can occur. Thirst is also controlled by the hypothalamus. Stimulation can cause drinking while damage to it can decrease fluid intake. Emotional reactions are controlled by the hypothalamus. Stimulation of the hypothalamic and amygdaloid nuclei can produce a fear reaction 30. Rage responses are noted after removal of the ventromedial areas or by stimulating an area in the lateral hypothalamus. There is also a part of the posterior portion which when stimulated produces an avoidance behavior by the subject (i.e. demotivates). By comparing the aforementioned PMS symptomatology with the hypothalamic functions described, a correlation is suggested (FIG. 8). In FIG. 8, symptoms seen in PMS are related to the types of responses and behaviors previously described for the various areas of the hypothalamus. For example, anorexia and changes in appetite are frequent symptoms. As mentioned, the hypothalamus can produce excessive appetite or anorexia depending on the area stimulated 29. In a particular patient, some hypothalamic area may be stimulated to a greater or lesser degree and cause excessive eating or loss of appetite. Similarly, defensive behavior, fear, rage and motivation, can be linked with the activation of hypothalamic centers to produce the changes of irritability, labile mood, anger or decreased motivation 30. Therefore, these recognized hypothalamic functions and the scientific support for the role of ovarian hormones in modulating the Ang receptors of the hypothalamic and associated loci strongly supports the hypothesis that this may be the mechanism by which we link cyclic ovarian changes to the behavioral, cognitive and physical symptoms of PMS.

If Ang II and AT1 receptors modulate the symptoms of PMS then by intervening to modifying their function, we should effect a clinical improvement or change. In order to validate this hypothesis, a human clinical study is necessary. There are two ways to modify the activity of these ovarian hormone responsive AT1 receptors. Use of an angiotensin converting enzyme inhibitor (ACE I) reduces the production and subsequently the levels of circulating Ang II. A second preferred method is to utilize a specific AT1 antagonist which reduces the ability of circulating Ang II to bind and activate the receptor. A study utilizing an ACE I shows (preliminary data-unblinded assessment of groups) a beneficial effect in one group of patients. The side-effects of ACE I therapy have in some cases prevented continued therapy (ie chronic cough). Also ACE I drugs can cause fetal abnormalities and even death; therefore they must be used cautiously in subjects who may wish to become pregnant.

The use of AT1 antagonist is not associated with a chronic cough and should be better tolerated by patients. In addition, no adverse fetal effects have been described from these agents.

In summary, there is strong evidence to support the role of ovarian hormones in modulating the activity of AT1 receptors. These AT1 receptors and neurons which utilize Ang II as a neurotransmitter, are located in areas of the hypothalamus and central nervous system which can medicare many of the physiologic responses and subsequent symptoms seen in the course of Premenstrual Syndrome. Finally, in a clinical study, data are emerging, suggesting that by reducing the levels of Ang II, and activation of AT1 we can modulate the symptoms of PMS. Therefore, I request that this patent be granted for the utilization of AT1 antagonists to treat the Premenstrual Syndrome.

I claim:

1. A method of treating PMS comprising administering to a female during the luteal phase or symptomatic period of a menstrual cycle an effective amount of an $AT_1$ antagonist.

2. The method of claim 1, in which said administering includes administering at least one $AT_1$ antagonist orally in an amount from about 0.5 mg to about 500 mg. over a period of about twenty-four hours during the luteal phase of the menstrual cycle.

3. The method of claim 1 in which said administering includes administering of losartan as said $AT_1$ antagonist.

4. The method of claim 1 wherein said $AT_1$ antagonist is selected from the group consisting of 2-n-butyl-4-chloro-5-hydroxymethyl-1-{2(1H-tetrazol-5-yl) biphenyl- 4-yl-methyl} imidazole-;(1H-imidazole-5-carboxylic acid, 4-(pentafluoroethyl)-2-propyl-1-[[2'-(1H-tetrazol-5yl ) [1,1'-biphenyl]- 4-yl]methyl]); (4'[(1,4-dimethyl-2'-propyl [2-b'-bi-1H-benzimidazol]-1'-yl)methyl]-[1,1'-biphenyl]-2-carboxylic acid); RWJ-38970; (2-carbethoxymethylidene-4-methyl- 4-ethyl-2-[4-(2'-tetrazolo)-phenyl] benzylpiperidin-6-one); (2,7-diethyl-5-[2'-(5-tetrazolyl)biphenyl-4-yl] methyl]-5H-pyrazolo[ 1,5-yl)biphenyl-4-yl methyl]-1,2,3,4-tetrahydro- 1,6-naphthyridin-2-one HCl); L-159878; L-158809; SC-51316; SC-51895; (3-[2-butyl-1-(4-carboxybenzyl)1H-imidazol-5-yl]-2-(2-thienylmethyl)-2-(E)-propenoic acid); UP-269-6; ((S) -N-valeryl-N-([2'-(1H-tetrazol-5-yl-biphenyl-4-yl]methyl)-valine); CGP-48369, (an angiotensin II antagonist); CGP-48369; WAY-126227; ZD-8731; KT-3671; and (2-n-butyl- 4-spirocyclopentane-1-[((2'-tetrazol- 5-yl)biphenyl-4-yl)methyl]-2-imidazolin-5-one) pharmacologically acceptable salts and mixtures thereof.

5. The method of claim 1 wherein said $AT_1$ antagonist is administered in combination with a diuretic.

6. The method of claim 5 wherein said diuretic is selected from the group consisting of hydrochlorothiazide, chlorthalidone, chlorthiazide and mixtures thereof.

7. A method of treating PMS by administering an effective amount of an $AT_1$ antagonist during a 24 hour period proximal to the luteal phase or symptomatic period of each menstrual cycle.

* * * * *